United States Patent [19]
Sit'ko

[11] Patent Number: 5,507,791
[45] Date of Patent: Apr. 16, 1996

[54] MICROWAVE RESONANCE THERAPY

[76] Inventor: Sergei P. Sit'ko, 61-B Volodymytska St, Kiev, 252033, Ukraine

[21] Appl. No.: 297,748

[22] Filed: Aug. 30, 1994

[30] Foreign Application Priority Data

Aug. 31, 1993 [UA] Ukraine .................. 93121771

[51] Int. Cl.$^6$ .................................... A61N 5/02
[52] U.S. Cl. .................... 607/101; 607/156; 128/898
[58] Field of Search ................... 128/898, 907, 128/735; 607/101, 46, 45, 156

[56] References Cited

U.S. PATENT DOCUMENTS

| | | |
|---|---|---|
| 676,332 | 6/1901 | Marconi . |
| 2,642,529 | 6/1953 | Frankel . |
| 4,334,229 | 6/1982 | Boblett . |
| 5,131,409 | 7/1992 | Lobarev et al. . |
| 5,152,286 | 10/1992 | Sitko et al. . |
| 5,195,517 | 3/1993 | Chen .................................... 607/45 |

FOREIGN PATENT DOCUMENTS 2203944  11/1988  United Kingdom ........... 128/907

OTHER PUBLICATIONS

Sit'ko, et al., *Introduction to Quatum Medicine*, 1994, pp. 1–126.
*Physics of the Alive*, vol. 1, No. 1, 1993, pp. 1–143, edited by Prof. Sergei Sit'ko, including eleven individual papers.
Vidhuk brochure, *Interbranch Scientific and Engineering Center on Physics of the Alive and Microwave Resonance Therapy, Profiles of Professional Activities*.
Vidhuk brochure, *Vidhuk Interbranch Scientific and Engineering Center on Physics of the Alive and Microwave Resonance Therapy*.
"Physics of the Alive and Microwave Resonance Therapy," Proceedings of the Colloquium on Microwave Resonance Therapy held in Ghent, May 19–25, 1994.
Y. A. Andreev et al., "Response of Human Organism to EHF–radiation Electromagnetic Fields," U.S.S.R. Academy of Sciences Bulletin No. 1, 1986, pp. 24–32.
S. P. Sitko, et al., "The Whole as a Result of Self–Organization," *Journal of Biological Physics*, vol. 18, (1991), pp. 1–10.
S. P. Sitko, et al., "Towards a Quantum Physics of the Living State," *Journal of Biological Physics, vol. 18, (1991), pp. 1–10*.
J. Manning, "Electroacupuncture," *Impressum*, vol. 2, No. 2, 1990/1991, pp. 64–65.

"Bioengergizer (MRT)–Lightning in Your Hand," Advertizement/Article, Robert C. Beck, 1990.
"Abstract of the First Symposium on the Fundamental Aspects of the Application of mm–Range Electromagnetic Radiation in Medicine," Council of Ministers of Ukr SSR, relating to a May 10–13, 1989 Symposium in Kiev, Ukraine.
"New Directions for Medicine . . . Focussing on Solutions," Professor Sitko spoke at this Oct. 5–7, 1990 conference at the Warner Center Marriott Hotel in California (note discussion on of MRT p. 3 and Prof. Sit'ko's biography and the discussion on pp. 5 and 7).
European Academy of Childhood Disability, Second Meeting of St Hild & St Bede, Durham, Sep. 2–4, 1990 (Prof. Sitko spoke at this conference).
Newspaper Article about Professor Sitko, published more than one year from the filing date of this application.
"Microwave Resonance Therapy," a brochure from SRC, Vidguk, Kiev, USSR relating to microwave resonance therapy and devices used for this treatment.

*Primary Examiner*—Lee S. Cohen
*Attorney, Agent, or Firm*—Beveridge, DeGrandi, Weilacher & Young

[57] ABSTRACT

The invention relates to a method of treating primarily functional disturbances like dyskinesias, vegetative dystonies, dishormonoses, parethes and reversible organic damages of human organism, e.g., gastric or duodenal ulcer, osteochondropathies, similar osteo-articular diseases, tissue damages, including wounds made with cold or firearms, etc., by means of acting on biologically active (acupuncture) points (BAPs) with low power (nonthermal) electromagnetic radiation of extremely high (EHF) frequency. A first subset of BAPs are defined on the basis of a preliminary diagnosis of the set of biologically active points (BATs) which are potentially able to result in therapeutical effects. At least on BAP from the first subset is subjected to millimeter electromagnetic radiation with a gradual alteration of its frequency and power density ($10^{-20}$ W/Hz-cm$^2$ to $10^{-10}$ W/Hz-cm$^2$) to provide a steady responsive reaction in the damaged areas. The first subset of BAPs are alternatingly treated by irradiating at the characteristic frequency determined in the previous step. Once the patient's sensor reactions cease from treatment of the first subset of BAPs, a second subset of BAPs is selected, and the treatment process is repeated decreasing the power density. The BAPs are meridionally connected with the damaged organ. Preferably, the chiral sensitivity of the patient's organism is determined, and the treatments include irradiation with electromagnetic radiation polarized in accordance with the chiral sensitivity of patient's organism.

5 Claims, No Drawings

MICROWAVE RESONANCE THERAPY

BACKGROUND OF THE INVENTION

The invention relates to a method for treating primarily functional disturbances like dyskinesias, vegetative dystonies, dishormonoses, parethes and reversible organic damage of human organism, e.g., gastric or duodenal ulcers, osteochondropathies, similar osteo-articular diseases, tissue damage, including wounds made with cold or firearms, etc., by means of acting on biologically active (acupuncture) points (abbreviated further as "BAPs") with low power (nonthermal) electromagnetic radiation of extremely high frequency (EHF).

In this specification, hereinafter the terms "EHF electromagnetic radiation" and "microwave radiation" are regarded to be synonyms.

The potential of EHF electromagnetic waves for application as a medical treatment was established rather long ago. However, its interaction with living cells, cell structures and the organism as a whole remains the subject of active experimental and theoretical investigation (see, for instance, Andreyev Ye.A., Bely M.U., Sit'ko S.P., "Reaction of Human Organism on the Electromagnetic Radiation of Millimeter Range," *Vestnik Academia Nauk SSSR*, 1985, 1, 24–32 (in Russian); and Andreyev Ye.A., Bely M.U., Sit'ko S.P., "Manifestation of Characteristic Eigenfrequencies of Human Organism," *Dopovidi AN UkrSSR B*, 1984, 10, 56–59 (in Ukrainian)). These documents are each entirely incorporated herein by reference.

Particularly, in the first of the mentioned articles, it was stated that healthy men typically do not react upon the millimeter range electromagnetic radiation (27–78 GHz, the power density below 10,000 $\mu W/cm^2$), while persons who are ill, after being subjected to the irradiation of strictly specified areas of their body with electromagnetic waves of fixed frequency ranging from 45 to 65 GHz, demonstrate expressive sensor reactions like warmth, coldness, pricking feelings, local or diffuse pains, or parethesias in the areas of the diseased organ's arrangement. Typically, the location of the diseased organ is spaced a distance from the zone of irradiation. It was shown there that for some frequencies of this range, the organism displays a general reaction in the form of an emotional rise (esophoria), or conversely, inhibition (sleepiness), and that sensor reactions in many cases tightly (resonancely) respond to definite (named further "characteristic") (eigen) frequencies, the deviation of which by less than 1% results in the loss of the aforesaid responses. It was further shown that the arrangement of the areas of the human organism maximally sensitive to EHF electromagnetic radiation (EMR) corresponds to the layout of acupuncture BAPs.

In view of this data, and because EHF electromagnetic radiation is intensively absorbed by cell water, making it practically impossible at present to directly physically register the aforesaid dependencies between the psycho-physiological reactions of the human organism and the frequency of the radiation, two main conclusions have been made:

it is the sensory reactions of patients that are best used in prescribing treatment and monitoring its course (particularly in view of the fact that positive (therapeutic) effects result only at characteristic frequencies accompanied by comfort feelings, i.e., pain reduction, local warmth, muscle relaxation, the feeling of elation, etc.); and the organism itself must choose the required characteristic frequencies.

The last conclusion was practically realized with the creation of a spark ("noise") generator of wide range EHF electromagnetic radiation (see the description of the invention in U.S. Pat. No. 5,152,286, which patent is entirely incorporated herein by reference), the use of which for microwave resonance therapy envisaged irradiation of BAPs selected for treatment during a definite (from several minutes to several tens of minutes) period of time. It was demonstrated that the patient's organism can itself choose the necessary (resonance) narrow band subranges of characteristic frequencies from a wide band of electromagnetic "noise."

In such cases, however, the selection of definite BAPs for medical treatment was made using classical ideas, rooted in the traditional (zheng-quy) therapy, that acupuncture points are linked with concrete organs or systems of the human organism. It is natural that the psycho-physiological state of definite patients and personal peculiarities of their reactions to the provided treatment were taken into account insufficiently, and as a result, in many cases, a positive result of the treatment proved to be problematic. Moreover, during the treatment with the help of the above device, most of its exit power was uselessly spent inducing electromagnetic "pollution" of the environment around the patient or medical workers, with unknown and uncertain consequences for them.

Therefore, in microwave resonance therapy, an accent was made on the selection of resonance characteristic (eigen) frequencies controlled by a physician. One such device for performing microwave resonance therapy is described in U.S. Pat. No. 5,131,409, which patent is entirely incorporated herein by reference.

From a number of methods based on this principle, the one closest to the proposed method is that of microwave resonance (reflex) therapy known from the description of invention in the USSR certificate of authorship and in the Russian Federation Patent No. 1 341 762. This Russian Federation Patent document is entirely incorporated herein by reference.

This method provides:

definition, on the basis of preliminary diagnosis, of an initial set of BAPs (acupuncture points), the action on which may induce therapeutical effects;

determination of a subset (in the form of a specified short list) of BAPs, action on which induces positive sensor reactions, and therefore can actually ensure therapeutical effects, including:

probing each of the previously chosen BAPs with EHF electromagnetic radiation, gradually varying the frequency in the 40–70 GHz range and the power density in the 10 to 10,000 $\mu W/cm^2$ range;

definition of at least one characteristic frequency and one minimum power density for which a steady sensor reaction of the patient's organism is observed in the damaged zone;

selection of BAPs, the action on which leads to positive sensor reactions of the patient's organism (such list of BAPs is often named "the prescription," by analogy with drug treatment);

the course of treatment by EHF electromagnetic irradiation of the selected BAPs (usually the seance's duration is 30–60 minutes daily or every other day), with the alternation of BAPs and the characteristic frequencies corresponding to them from seance to seance, and (in the case of positive sensor reaction reduction) gradual increase of the power density from the established minimum in the range of 10 to 10,000 µW/cm$^2$ to the upper limit of 10,000 µW/cm$^2$; and control of the course of treatment according to the patient's description of his sensor reactions, and the termination of the treatment when sensor reactions in the area of damage are lost at the maximum power density of 10,000 µW/cm$^2$.

The change of BAPs in the course of a seance is also possible within the scope of the prescription, as well as termination of a seance following the appearance of pain or other discomfort sensations in a patient.

However, even at a power density as low as 8000 µW/cm$^2$, along with the therapeutical effects, there appears a thermal effect of the EHF electromagnetic radiation on the BAPs and the adjacent tissues (this effect may enhance with a further increase of power density and time of exposure). This results in a weakening of the therapeutical action and may: (1) induce the above mentioned discomfort feelings in a patient during medical seances, (2) lead to far from optimal use of the potential of the BAPs chosen at the beginning of the treatment, and (3) ensure mistakes in determining the terms of treatment termination.

Moreover, the seance to seance increase of the power density of EHF electromagnetic radiation (e.g., radiation having extremely hard and clearly expressed general biological effect) may result in hardly foreseeable negative consequences for the patient's organism as a whole, particularly in the case where the time of exposure is up to 60 minutes.

However, while applying microwave resonance therapy, it is important to decrease the effective dose absorbed in every course of treatment, particularly when there is a need for several consequential courses of treatment.

Finally, the sensitivity of individual patients to the therapeutic action of EHF EMR and, respectively, the necessity to have definite effective absorbed doses of this radiation for the therapeutical effect to become evident, depend not only on the type of disease and the general psycho-physiological status of the organism, but also on such peculiarities of the organism's biochemical status as chirality (i.e., the left or right rotation of the EMR, or the type of protein or other macromolecules in the biotissues), and, respectively, different sensitivity of concrete patients to the left or right polarized microwave radiation.

In connection with the aforesaid, at the basis of the invention there was the task to improve the sequential arrangement and adjust regimens or treatment methods in order to create such a method of microwave resonance therapy that would lower the effective absorbed dose in the course of treatment, and at the same time, take into account the chiral sensitivity of patients, thereby accelerating therapeutical effects.

SUMMARY OF THE INVENTION

The invention relates to a method of treating a patient with microwave resonance therapy. In this method, a set of biologically active points are defined on the basis of a preliminary diagnosis, wherein action on the biologically active points is potentially able to result in therapeutical effects. A first subset of the biologically active points is selected, and at least one biologically active point of the first subset is subjected to millimeter electromagnetic radiation with a gradual change of its frequency and power density from $10^{-20}$ W/Hz-cm$^2$ to $10^{-10}$ W/Hz-cm$^2$ so as to determine at least one characteristic frequency and one minimum level of power density which provide steady responsive reactions in the patient's organism in an area of damage. Thereafter, the biologically active points of the first subset are treated by irradiating with electromagnetic radiation of the characteristic frequency. The patient's responses to the treatment are indexed, and the treatment is repeated in successive seances until the responses in the area of damage have stopped. During treatment, the biologically active points of the first subset are irradiated in an alternating manner in each treatment, wherein the power density level does not exceed a minimum level at which, during the step of subjecting at least one biologically active point of the first subset to electromagnetic radiation, positive responses are observed in the patient. Once positive responses stop in the first subset of biologically active points, a second subset of biologically active points is selected, and at least one biologically active point of the second subset is subjected to millimeter electromagnetic radiation with a gradual change of frequency and power density so as to determine at least at one characteristic frequency and one minimum level of power density which provide steady responsive reactions of the patient's organism in the area of damage. The second subset of BAPs may be selected completely from the originally defined set of BAPs. However, this second subset of BAPs need not include BAPs which were part of the originally defined set of BAPs. Other BAPs which are not part of the originally defined set of BAPs may be selected, depending on the patient's response to treatment. Biologically active points of the second subset are then treated by irradiating with electromagnetic radiation, wherein biologically active points of the second subset are irradiated in an alternating manner in each treatment at the characteristic frequency, and the power density level does not exceed the minimum level.

In the process in accordance with the invention, the first subset of biologically active points may be arbitrarily selected from a general set of biologically active points connected meridionally with the area of damage, while the second subset of biologically active points is selected based on an index of maximum painfulness during irritation.

In another embodiment of the invention, a specific second subset of BAPs is not selected for repeated treatments. An initial, primary set of BAPs is selected using classical acupuncture diagnosis techniques known to those skilled in the art. Prior to every seance, and preferably even during the seance procedure, the status of the individual BAPs is checked (e.g., the patient's response to irritation and/or palpitation of the BAPs or a verbal description of their response to treatment) such that successive sets of BAPs which are subjected to treatment are defined depending on the patient's reactions or responses to the treatment. In this way, not only the primary BAPs selected by classical acupuncture diagnosis are treated, but, in principle, treatment may be expanded to the whole map of BAPs. Such continuous updating of the treated BAP sets can allow maximum treatment response while minimizing the radiation to which the patient is exposed.

Advantageously, the process of the invention may include a step of determining chiral sensitivity of the patient's organism, wherein the electromagnetic radiation used in the treating steps is polarized based on the results of the chiral sensitivity determination. Chiral sensitivity may be determined in accordance with the patient's maximum responses in at least one arbitrary biologically active point by alternatively acting upon it with differently polarized electromagnetic radiation.

DETAILED DESCRIPTION OF THE INVENTION

The method of microwave resonance therapy, including the action on biologically active points (acupuncture points) by millimeter range electromagnetic radiation, is distinguished in such a way, with the aim of efficacy of treatment, to improve the recovery of all of the meridional system ("electromagnetic frame") of organism. Prior to the treatment, using the available methods of traditional diagnosis (e.g., thermovision) and acupuncture diagnosis (e.g., Folle-Riadaraki method) and/or being ruled by analysis of the patient's description of his sensor reactions under palpation, one selects the meridians with damaged functioning for the action upon the biologically active points of the symmetrical meridians in the beginning of the treatment. This treatment procedure mentioned above is repeated prior to each seance, and the treatment must be continued until complete recovery of meridional system takes place.

Under the guidance of the responsive reactions of the human organism as a whole and controlling the dynamics of the meridional system functioning, one acts on biologically active points (primarily of distal type) using therapeutical frequencies (determined by standard methods) and selecting the optimal wave characteristics, i.e., frequency, level of monochromathy, coherency, type of polarization (left or right), with subsequent power decrease from 100 $\mu$W/cm$^2$ to the quantum limit ($\approx 10^{-20}$ W/Hz-cm$^2$) to enhance the organism's sensitivity.

Each biologically active point is irradiated (exposition) for a time defined according to the dynamics of the meridional system state. Typically, the time is set in the range of 20 seconds to 3 minutes. The duration of the treatment of each BAP during a seance depends on the dynamics of the treatment. For example, if during treatment the patient indicates that the pain is gone, or if uncomfortable reactions are eliminated on the palpitation of the area of the BAP symmetric to the BAP being irradiated, treatment may be terminated. Control for the results of treatment is carried out with available methods of medical diagnosis.

The solution of the task was found in a method of microwave resonance therapy that involves defining, on the basis of a preliminary diagnosis, the set of biologically active points (BAPs), the action on which is potentially able to result in therapeutical effects. A subset of BAPs is selected which, when subjected to millimeter electromagnetic radiation with a gradual alteration of its frequency and power density to the level of no more than 100 $\mu$W/cm$^2$, display at least at one characteristic frequency and one minimal level of power density which results in steady sensor reactions of the organism in the damaged areas. Treatment in the form of several seances of microwave irradiation of selected BAPs using the characteristic frequencies and alternating BAPs follows. The course of treatment is controlled according to the patient's description of his or her sensor reactions, wherein the treatment is terminated when sensor reactions cease in the area of damage. According to the invention, the selected BAPs are alternated in every seance and are subjected to the action of EMR with power density levels not exceeding the minimums on which positive sensor reactions occurred in the course of the selection of BAPs subsets. Sensor reaction reduction is monitored from seance to seance, and after the seance during which the sensor reaction stopped, a next subset of BAPs is determined which, when subjected to millimeter electromagnetic radiation with a gradual alteration of its frequency and power density, display at least one characteristic frequency and one minimal level of power density which results in steady sensor reactions of the patient's organism in the area of damage. The BAPs from this next subset are irradiated with millimeter radiation while being alternated during every seance, using the characteristic frequencies and power density levels not exceeding the established minimums.

Typically, during the courses of treatment, seances are run every day for 10–12 days, and a gap between the first and second treatment courses is typically about one month.

As is evident from the above description of the invention, the treatment is carried out with minimal radiation loading on the patient's organism during all the seances, and this technical result is achieved only under a condition of using at least two alternations of BAP subsets from which the concrete acupuncture points are selected for the treatment. As the technical result is supersummary, the repetition of the list formation procedures and consequent medical treatments does not logically ensure from the known level of technology, and the invention as a whole may be considered as meeting the requirements of patentability for invention status.

One distinguishing characteristic of the invention is that the first subset of BAPs is arbitrarily selected from the total set of BAPs meridionally connected with the damaged organ. The consequent subsets of BAPs is taken from the BAP subsets left out in the first and each of the previous subset selections, using the index of the maximum painfulness under the irritation. In this manner, the treatment process involves the maximum number of channels which may effect the damaged organ, which exercises additional positive influence on the speed of the formation and stability of therapeutical action.

In this application, the term "index of maximum painfulness" means that several (or all) of the BAP points connected to a damaged organ are subjected to irritation and/or palpitation. The patient's response to this irritation and/or palpitation is recorded and indexed. In this way, the BAPs connected to the organ which provide a maximum response may be identified.

Another distinguishing characteristic is that prior to the first seance, the chiral sensitivity of the patient's organism may be tested. Thereafter, in further treatment seances, use is made of electromagnetic radiation polarized in accordance with the chirality revealed. This additionally lowers the effective absorbed dose and favorably influences the speed of the achievement, completeness and stability of curative effect.

An additional distinguishing characteristic of the invention is that the chiral sensitivity of the patient's organism is determined by subjecting at least one arbitrary BAP to differently polarized electromagnetic radiation, and then determining which type of electromagnetic radiation induced the maximum sensor reaction in the organism. This way of the chiral sensitivity definition is the most proper for the applied method of treatment in question, because it does not require any additional devices.

The proposed method of microwave resonance therapy is generally realized in the following way.

After the preliminary diagnosis based on the anamnesis and/or objective examination of the patient, manuals for zheng-quy-therapy or data bases (in particular automatic databases) for microwave resonance therapy are consulted to define the set (the total list) of biologically active points (BAPs) connected meridionally with the damaged organ, which when acted upon with EHF electromagnetic radiation may potentially bring about therapeutical effect. Out of this set, e.g., using the criterion of the highest susceptibility to palpation or other irritation, or arbitrarily, proceeding from previous medical experience, a first subset (the first concrete list) of BAPs is chosen.

Then using one of the apparatuses for microwave resonance therapy, particularly model AMRT-02 (available at VIDHUK in the Ukraine), which allows one to gradually alter frequencies at least in the range of 52–62 GHz and gradually alter power density in the range from the upper level of 100 $\mu W/cm^2$ to the lower level of practical quantum limit (with the help of attenuators), at least one of the BAPs of the first subset is probed with electromagnetic radiation of the millimeter range, changing its frequency and power density in order to determine at least one characteristic (resonance) frequency and one minimum power density at which a steady (comfort) sensor reaction of the patient's organism in the area of damage is observed.

Then, the first stage of treatment is realized using the BAPs of the above mentioned first subset. This first treatment stage of the first subset of BAPs constitutes the first "prescription."

This stage includes: several seances of EHF electromagnetic irradiation of the selected BAPs using the previously defined characteristic frequencies and power density not exceeding the minimums under which the sensor reactions are observed, and alternating all of the selected BAPs during each seance. The course of treatment is controlled according to the patient's description of his sensor reactions and their intensity, and the moment is determined when these reactions cease at the acupuncture points from the first subset of BAPs (the first prescription). After the seance in the course of which the cessation of the sensor reaction is revealed, a second subset of BAPs is chosen using the aforesaid criterion of maximal pain reaction to irritation from the general initial set of BAPs meridionally connected with the damaged organ. The second subset of BAPs (the second prescription) is probed as mentioned above, i.e., using gradual alteration of the frequency and power density of EHF (microwave) electromagnetic radiation, to define for this subset at least one characteristic frequency and one minimum power density at which steady positive sensor reactions are observed. This second prescription of BAPs is subjected to microwave radiation in the course several seances, alternating in each seance, using the characteristic frequencies and power density levels which do not exceed the established minimums. The presence and intensity of sensor reactions is monitored in the area of the damaged organ.

While controlling the course of treatment according to the weakening of the sensor reactions in the second prescription, third and consequent prescriptions may be made, if the need arises, until the list of BAPs meridionally connected with the damaged organ is exhausted. At that time, the treatment is terminated.

To enhance the patient's organism sensitivity to its therapeutical effect, preferably the microwave electromagnetic radiation is polarized and applied at each of the prescribed BAPs with the polarity corresponding to the chiral sensitivity of the patient. The chiral sensitivity is determined based on the maximum of the organism's sensor reaction induced in at least one arbitrarily selected BAP after subjecting it to differently polarized electromagnetic radiation.

The essence and the advantages of the proposed method will become clear in more detail from the examples mentioned below, which were taken from several disease histories.

EXAMPLE 1

Patient K, 37 years old (disease history No. 9014), entered the neurological hospital with the diagnosis: diffuse osteochondrosis, the secondary radicular syndrome with the expressive pain reaction.

Previous courses of medicamentous and physiotherapeutic treatment failed to produce visible positive effects.

Proceeding from the preliminary diagnosis and in accordance with the recommendations of "Guidance for Acupuncture" edited by Macheret El. Kiev: Vyscha shcola (1988) (which document is entirely incorporated herein by reference), the initial set (general list) of BAPs meridionally connected with the vertebral or nervous plexuses of lumbar and arvicothoracal areas was selected which could potentially be efficient if acted upon: namely points: E36, V44, V60, T3, T4, G14, RP1, RP6, and R2.

These BAPs were palpatively investigated and according to the maximum painfulness criterion, the first prescription was prescribed including points V60, RP6, R2 and T3 from the list mentioned above. In addition, based on earlier medical experience, it was revealed that the meridians of the bladder, kidneys, spleen, and pancreas also were malfunctioning.

Using the aforementioned device for microwave resonance therapy (AMRT-02 model), point RP6 was acted upon with gradually altering frequency and power density (with the use of attenuators), and the characteristic (resonance) frequency of 61.4 GHz and minimal power density of 0.1 $\mu W/cm^2$ were determined. A positive sensor reaction was induced in the form of wavy movements in the back group of femoral muscles and a feeling of warmth in the lumbar area was established.

As is known from experience in microwave therapy, the acupuncture points connected with a malfunctioning organ react in a similar way—i.e., at the same characteristic frequencies and the same power density—to the millimeter range electromagnetic radiation. Therefore, points specified in the first prescription were subjected to the action of the same characteristic frequency and power density shown above, without exceeding the above mentioned level, and while alternating to different BAPs during every seance. The patient's sensor reactions were monitored. According to the patient's descriptions, weakening of the above mentioned sensor reactions took place by the end of the fourth seance.

Then, within the limits of the previously selected BAPs, palpative examination was carried out, and according to the results thereof, the second subset including the points V44, RP9, J2 was assigned. Following the probing of RP9 point according to the method described above, the characteristic frequency 60.12 GHz and minimum power density of 0.01 $\mu W/cm^2$ were determined, and in the same way, the second stage of treatment consisting of three seances was provided.

By the end of the seventh seance, the sensor reactions disappeared, the patient's state essentially improved and the disease's symptoms ceased completely, although besides the medical improvement in the course of seances, close to the end, a side effect was also detected in the form of weak dull pains in the occipital area. These pains ceased when the power density of the microwave radiation was reduced with the aid of attenuators.

During the control examinations 1, 3 and 6 months later, relapses were not observed.

Each seance duration was 15–20 minutes.

EXAMPLE 2

Patient I, 53 years old (disease history no. 14371) entered the hospital with postthyreotoxical encephalophtalmopathy and complains about systematic and hardly bearable headaches, insomnia, diplopia, acute eye pain and depraved vision.

Proceeding from the preliminary diagnosis and using recommendations from the Automatic System of the Physician Decisions Support, a set of BAPs was selected including acupuncture points VB1, RP1, RP3, V65, T14, and MC5.

On the basis of previous medical experience, the first subset was designated that included points RP1, VB1, and T14. Using the method described in Example 1, point RP1 was probed, and the characteristic frequency of 60.31 GHz and a minimum power density of 0.001 $\mu W/cm^2$ were established which provided a positive sensor reaction in the form of wavy movements and a feeling of warmth in the eye sockets.

Additionally, by the consequent change of polarizers during the action on the same point, it was found that the left-polarized microwave electromagnetic radiation essentially enhanced the sensor reaction. Therefore, further treatment was carried out in a manner similar to the first example, with a distinction ensuing from the chiral sensitivity of the patient's organism.

By the end of the fourth seance, a relaxation of sensor reactions in all the points of the first prescription was detected, along with an insufficient improvement of the patient's state. Therefore, according to the results of electrocutaneous conductivity, the second subset of BAPs was determined in the form of the points V60, RP6, and E1, and by probing point RP6, the above mentioned characteristic frequency and power density minimum were confirmed.

The second stage of the treatment with left-polarized electromagnetic radiation of the above mentioned frequency and power density, accompanied by the monitoring of the established positive sensor reactions intensity, also consisted of four seances during which relaxation of aforesaid reactions occurred, and the symptoms of the disease disappeared.

The result of the treatment was considered successful according to the complete examination data. Further check-up 3 and 6 months later revealed no complaints from I.

The duration of each seance was 15–18 minutes.

EXAMPLE 3

Patient A, 49 years old (disease history no. 1308) entered the hospital with varicose veins complicated by the post-thrombophlebitis syndrome with extended trophic ulcers and complaints about pain in the lower extremities, edemas and abundant purulent discharge from the ulcers.

During the examination, it was found that the ulcers were situated in the lower third of the left cruse and had dimensions 8×10 and 3×5 cm, in irregular form with digged edges, and the bottom was covered with the necrotic masses and fibrin.

In accordance with the "Guidance for Acupuncture" mentioned above in Example 1, the set of BAPs including the points E36, G14, T4, V60, and TR5 was determined.

The subset including points E36, T4 and TR5 was chosen according to the evaluation of painfulness under palpation. As was described in the first example, for point E36 a characteristic frequency of 59.37 GHz and a power density minimum of $0.1\times10^{-12}$ $\mu W/cm^2$ were determined, and the treatment with microwave irradiation of the depicted points using alternation during each seance began. Each seance lasted 20–25 minutes.

By the end of the fifth seance, positive sensor reactions in the form of warmth in the ulcer area practically ceased, while improvement of the patient's state became visible: a reduction of pain in the extremities, a cessation of the edema and skin hyperemia in the paraulcerous area, and active granulation.

Further using the method of electrocutaneous conductivity measurement, the second subset of active points was found, two of which (E36 and T4) were also components of the first subset, and the third, V60 which was not used earlier. By probing the V60 point, the above-mentioned characteristic frequency and minimum power density were confirmed. The second stage of microwave resonance therapy, which also consisted of five seances, was carried out with the alternation of irradiated points during every seance. The intensity of the sensor reaction and the state of the area of trophic ulcers localization were observed.

By the end of the fifth seance of the second stage, the ulcers were cleaned of the necrotic masses, the bottom was performed with granulations, and, as a result of active edge epitalization, the size of the ulcers reduced more than twofold, and edema and pain ceased.

The patient left the hospital, and two weeks later a second supportive six seance course of treatment was carried out with action on the first prescription points using the above mentioned parameters.

In the course of control examinations a month after the second course of treatment, the ulcers cicatrization was revealed, and 3 and 6 months later firm cicatrix was found on its place.

At all the stages of treatment, microwave resonance therapy was used as a main method of treatment. Only local treatment of the wounds with antiseptics and water dressings were used.

The aforesaid examples do not exhaust the factual material summarized during the experimental testing of the method according to the invention. Therefore, below in the table, additional statistical data is shown relating to the results of the proposed method application in comparison with the earlier received analogous data of the method-prototype application.

| NAME OF DISEASE | RESULTS OF TREATMENT AND SIDE EFFECTS FREQUENCY[1] | | | |
|---|---|---|---|---|
| | Good (%) 1 | Satisfactory (%) 2 | Without Changes (%) 3 | Side Effects (%) 4 |
| Ulcer Duodenal | 95/67 | 5/20 | —/13 | 4/13 |
| Postoperation Paresis of Bladder | 93/72 | 7/12 | —/16 | 6/19 |
| Polyposis Gastrica | 78/60 | 22/31 | —/19 | 4/6 |

[1]In every column and line, the first figure before the slash means the efficacy of the method according to the invention, and the figure after the slash means the efficacy of the method-prototype.

As can be seen from the table, the application of the proposed method allows for a reduction of essentially (3–4) times the number of cases when microwave resonance therapy results in side effects and eliminates the cases where a medical effect does not appear at all, and increases markedly the number of cases with good results. These medical results give clear evidence that the reduction of the effective absorbed EHF electromagnetic radiation dose is beneficial for the patients.

EXAMPLE 4

Patient N, 42 years old, admitted for treatment on 12 Apr. 93 with the diagnosis of a left ovarian cyst having the dimensions of 8.1×9.1 cm.

The treatment was performed by applying radiation from an AMRT-02 generator with the installed output power density of electromagnetic waves at the generator head equal to 0.1 nw ($10^{-10}$ w) using a right-hand polarizer, attenuating the beam by 30 db (i.e., variable attenuation from 0 to 30 db (maximum)) and a complementary attenuator in 40 db (i.e., constant attenuation). Prescription and dosage were selected individually for the particular patient (BAP: S1—2 min.; S2—2 min; T3—3 min; PC-104—30 sec.).

After the first MRT treatment course, consisting of 10 seances, the dimensions of the cyst were diminished to 7.4×4.5 cm.

After the second MRT course according to the same prescription and time of action on each of the BAPs, the left ovarian cyst was completely resolved, which fact was confirmed during ultrasound investigation, as well as by the physical examination by a gynecologist.

EXAMPLE 5

Patient K, 34 years old, was admitted for treatment 18 Apr. 94 with the diagnosis of dysplasia of the neck of the uterus.

The treatment was performed by applying radiation from the AMRT-02 generator with an installed output power density of electromagnetic waves at the generator head equal to 0.1 nw ($10^{-10}$ w) using the left-hand polarizer, attenuating the beam by 30 db. Prescription and dosage were selected individually for the particular patient (BAP: S1—2 min; S2—2 min; R9—3 min; T4—2 min; J3—2 min; PC-104—30 sec.).

After the first treatment course consisting of 10 seances, isolated atypical cells were determined at a histologic examination of a smear. A second treatment course was carried out beginning from 21.05, according to the same prescription, and no pathology thereafter had been found at the histologic examination.

EXAMPLE 6

Patient SH, 67 years old, was admitted for treatment on 28 Feb. 94 with the diagnosis of residual effects of the acute cerebral circulation disturbances (ischemia in the area of the middle cerebral artery with the right hemiparesis, dysarthria and partial aphasia).

Prior to treatment: the patient is conscious, his position in bed is passive, he is able to turn over in bed only with the help of others, he is emotionally labile and aggressive. The muscular tonus is D>S (i.e., Right (dextra)>Left (sinistra)), muscular atrophy, as well as partial lower extremity muscular atrophy are observed. Finger-nose test is disturbed. The patient's speech contact is difficult, the answers given are indistinct, monotonous and monosyllabic. His memory is reduced and distraction is observed.

The treatment was performed by applying radiation from an AMRT-02 generator with the installed output power density of electromagnetic waves at the generator head, equal to 0.1 nw ($10^{-10}$ w) using the right-hand polarizer, attenuating the beam by 30 db and the complementary attenuator in 40 db. Prescription and dosage were individually selected for the particular patient (BAP: S1—1 min; V62—1 min; RP8—2 min; TRP—1 min; G14—1 min; TR15—2 min; T14—2 min; T21—30 sec.).

After the first and second treatment seances, the patient's position in bed became active with no aggressiveness observed. The motor function of the extremities improved, active movements in distal sections of the extremities enlarged on the right, and spasticity decreased. The muscular tonus D>S with the difference being insignificant, and coordination of movement improved.

After the third seance, the patient was turning over in bed without anybody's help. After the sixth seance, the patient moved across the ward independently, articulation was improved, speech appeared to be more free-and-easy and intelligible. There appeared to be no necessity to concentrate attention before uttering words. A month later, after the end of the treatment, the patient was able to go out into the street independently.

EXAMPLE 7

Patient C, 11 years old, was admitted on 28 Oct. 93 with the diagnosis of hemophilia.

The treatment was performed by applying radiation from the AMRT-02 generator with the installed output power density of electromagnetic waves at the generator head, equal to 0.1 nw ($10^{-10}$ w), using right-hand polarizer, attenuating the beam by 30 db and a complementary attenuator in 40 db.

The prescription and dosage were selected individually (BAP: S1—1 min; V56—1 min; S2—1 min; RP6—1 min; R1—1 min; T4—2 min; TR5—1 min; PC-104—30 sec.).

After the first treatment course, the duration of hemorrhage was diminished to 8 min, and the pain in the lower and upper extremities articulations was decreased.

The second treatment course was performed beginning from 17 Nov. 93 by applying the same prescription to the BAPs. The duration of hemorrhage thereafter was reduced to 7 min; positive dynamics were marked in the immunologic and cytochemical examination results. The length of remission increased.

EXAMPLE 8

Patient D (the monovular twin of the patient C), 11 years old, was admitted on 28 Oct. 93 with the diagnosis of hemophilia.

Treatment was performed by applying radiation from the AMRT-02 generator with the installed output power density of electromagnetic waves at the generator head, equal to 0.1 nw ($10^{-10}$ w), using left-hand polarizer attenuating the beam by 30 db.

The prescription and dosage were selected individually (BAP: S1—1 min; V56—1 min; S2—1 min; RP6—1 min; R1—1 min; T4—2 min; TR5—1 min; PC-104—30 sec.).

After the first treatment course, the duration of hemorrhage was reduced to 8 minutes, and the pain in the lower and upper extremities articulations decreased.

The second treatment course was performed beginning from 17 Nov. 93 by applying the same prescription to the BAPs. The duration of hemorrhage thereafter was reduced to 7 min, positive dynamics were marked in the immunologic and cytochemical examination results. The length of remission increased.

While the invention has been described in terms of specific embodiments and examples, those skilled in the art will appreciate that various modifications and changes can be made without departing from the spirit and scope of the invention.

The priority application, Ukraine Application No. 93121771, filed in the Ukraine on Aug. 31, 1993 (corresponding to Ukraine Patent No. 2615, registered Feb. 15, 1994), is relied on and entirely incorporated herein by reference.

I claim:

1. A method of treating a patient with microwave resonance therapy, comprising: defining a set of biologically active points on the basis of a preliminary diagnosis, wherein action on the biologically active points is potentially able to result in therapeutical effects; selecting a first subset of the biologically active points and subjecting at least one biologically active point of the first subset to millimeter electromagnetic radiation with a gradual change of its frequency and power density between $10^{-20}$ W/Hz-cm$^2$ to $10^{-10}$ W/Hz-cm$^2$ so as to determine a first characteristic frequency and a first minimum power density level which provide steady responsive reactions in the patient's organism in an area of damage; treating biologically active points of the first subset by irradiation with electromagnetic radiation of the first characteristic frequency; indexing the patient's responses to the treatment; repeating the treating step until the responses in the area of damage have stopped, wherein the biologically active points of the first subset are irradiated in an alternating manner in each treating step, wherein the power density level does not exceed the first minimum level at which positive responses are observed during the subjecting step; thereafter, selecting a second subset of biologically active points and subjecting at least one biologically active point of the second subset to millimeter electromagnetic radiation with a gradual change of frequency and power density so as to determine a second characteristic frequency and a second minimum power density level which provide steady responsive reactions of the patient's organism in the area of damage; and treating the biologically active points of the second subset by irradiation with electromagnetic radiation, wherein biologically active points of the second subset are irradiated in an alternating manner in each treating step at the second characteristic frequency, and the power density level does not exceed the second minimum level.

2. A method according to claim 1, wherein the first subset of biologically active points is arbitrarily selected from a general set of biologically active points connected meridionally with the area of damage, and the second subset of biologically active points is selected based on an index of maximum painfulness during irritation.

3. A method according to claim 1, further comprising determining chiral sensitivity of the patient's organism, wherein the electromagnetic radiation used in the treating steps is polarized based on the results of the chiral sensitivity determination.

4. A method according to claim 3, wherein the chiral sensitivity is determined in accordance with the patient's maximum responses at least in one arbitrary biologically active point by alternatively acting upon it with differently polarized electromagnetic radiation.

5. A method for treating a patient with microwave resonance therapy, comprising: defining a set of biologically active points on the basis of a preliminary diagnosis, wherein action on the biologically active points is potentially able to result in therapeutical effects; selecting a first subset of the biologically active points and subjecting at least one biologically active point of the first subset to millimeter electromagnetic radiation with a gradual change of its frequency and power density between $10^{-20}$ W/Hz-cm$^2$ to $10^{-10}$ W/Hz-cm$^2$ so as to determine at least one characteristic frequency and one minimum power density level which provide steady responsive reactions in the patient's organism in an area of damage; treating biologically active points of the first subset by irradiation with electromagnetic radiation of the characteristic frequency, wherein the biologically active points are irradiated during the treating step in an alternating manner, and wherein the power density level does not exceed the minimum level at which, during the subjecting step, positive responses are observed in the patient; indexing the patient's responses to the treatment; selecting biologically active points for a next treating step based on the index of the patient's responses and treating the selected biologically active points.

* * * * *